United States Patent
Kearney

(10) Patent No.: US 8,137,030 B2
(45) Date of Patent: *Mar. 20, 2012

(54) DISPOSAL OF SLURRY IN UNDERGROUND GEOLOGIC FORMATIONS

(75) Inventor: Raymond J. Kearney, Los Angeles, CA (US)

(73) Assignee: EnerTech Environmental, Inc., Atlanta, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/028,297

(22) Filed: Feb. 16, 2011

(65) Prior Publication Data

US 2011/0142541 A1    Jun. 16, 2011

Related U.S. Application Data

(62) Division of application No. 12/597,008, filed as application No. PCT/US2008/061529 on Nov. 11, 2009, now Pat. No. 7,905,683.

(60) Provisional application No. 60/926,709, filed on Apr. 27, 2007.

(51) Int. Cl.
*B09B 1/00* (2006.01)

(52) U.S. Cl. ..................................... 405/129.1

(58) Field of Classification Search ............... 405/129.1, 405/129.2; 166/266, 268
See application file for complete search history.

(56) References Cited

U.S. PATENT DOCUMENTS

| | | | |
|---|---|---|---|
| 3,335,798 A | 8/1967 | Querio et al. |
| 3,724,542 A | 4/1973 | Hamilton |
| 3,772,181 A | 11/1973 | Cole et al. |
| 4,126,519 A | 11/1978 | Murray |
| 4,217,211 A | 8/1980 | Crane |
| 4,477,257 A | 10/1984 | Koppelman et al. |
| 4,762,527 A | 8/1988 | Beshore et al. |
| 4,798,801 A | 1/1989 | Hitzman |
| 4,826,769 A | 5/1989 | Menger |
| 4,845,034 A | 7/1989 | Menger et al. |
| 4,973,194 A | 11/1990 | Peterson |
| 5,133,624 A | 7/1992 | Cahill |
| 5,226,749 A | 7/1993 | Perkins |
| 5,261,766 A | 11/1993 | Anderson |
| 5,282,980 A | 2/1994 | Kew et al. |
| 5,314,265 A | 5/1994 | Perkins et al. |
| 5,318,382 A | 6/1994 | Cahill |
| 5,356,540 A | 10/1994 | Khan et al. |
| 5,405,224 A | 4/1995 | Aubert et al. |
| 5,424,195 A | 6/1995 | Volkwein |
| 5,431,236 A | 7/1995 | Warren |

(Continued)

FOREIGN PATENT DOCUMENTS

EP    1 228 164    10/2004

(Continued)

OTHER PUBLICATIONS

Article—"An Introduction to Slurry Injection Technology for Disposal of Drilling Wastes", US Department of Energy, Sep. 2003.

(Continued)

*Primary Examiner* — John Kreck

(74) *Attorney, Agent, or Firm* — Faegre Baker Daniels LLP

(57) ABSTRACT

The current invention provides processes and apparatuses for introducing slurry into underground geological formations thereby disposing of the slurry, while also sequestering carbon dioxide and collecting methane from the slurry.

21 Claims, 3 Drawing Sheets

U.S. PATENT DOCUMENTS

| | | | |
|---|---|---|---|
| 5,463,164 | A | 10/1995 | Perkins |
| 5,484,231 | A | 1/1996 | Cannan et al. |
| 5,485,728 | A | 1/1996 | Dickinson |
| 5,489,740 | A | 2/1996 | Fletcher |
| 5,536,115 | A | 7/1996 | Keck |
| 5,589,603 | A | 12/1996 | Alexander et al. |
| 5,685,153 | A | 11/1997 | Dickinson et al. |
| 5,734,988 | A | 3/1998 | Alexander et al. |
| 5,922,204 | A | 7/1999 | Hunter et al. |
| 5,961,438 | A | 10/1999 | Ballantine et al. |
| 6,002,063 | A | 12/1999 | Bilak et al. |
| 6,103,191 | A | 8/2000 | Luker |
| 6,143,176 | A | 11/2000 | Nagamatsu et al. |
| 6,287,248 | B1 | 9/2001 | Bruno et al. |
| 6,409,650 | B2 | 6/2002 | Bruno et al. |
| 6,410,283 | B1 | 6/2002 | Rehmat et al. |
| 6,491,616 | B2 | 12/2002 | Bruno et al. |
| 6,962,561 | B2 | 11/2005 | Bruno et al. |
| 7,056,062 | B2 | 6/2006 | Takeuchi et al. |
| 7,069,990 | B1 | 7/2006 | Bilak |
| 7,097,386 | B2 | 8/2006 | Maduell et al. |
| 7,211,194 | B2 | 5/2007 | Titmas |
| 7,285,694 | B2 | 10/2007 | Countz |
| 7,905,683 | B2 * | 3/2011 | Kearney ............... 405/129.1 |
| 2002/0111527 | A1 | 8/2002 | Bruno et al. |
| 2005/0155930 | A1 | 7/2005 | Tunnacliffe et al. |
| 2006/0084833 | A1 | 4/2006 | Bruno et al. |
| 2006/0096163 | A1 | 5/2006 | Dickinson et al. |
| 2006/0178547 | A9 | 8/2006 | Bruno et al. |

FOREIGN PATENT DOCUMENTS

| | | |
|---|---|---|
| WO | 01/14015 | 3/2001 |

OTHER PUBLICATIONS

"Converting Biosolids to Energy by Deep Well Injection and Biodegradation", Canadian National Residuals and Biosolids Management Conference, Toronto, Ontario, Sep. 24-26, 2000.

"Terminal Island Renewable Energy Project", City of Los Angeles and Terralog Technologies, at least as early as Oct. 22, 2009.

* cited by examiner

FIG_1

DISPOSAL OF SLURRY IN UNDERGROUND GEOLOGIC FORMATIONS

CROSS-REFERENCE TO RELATED APPLICATIONS

This application is a continuation of U.S. patent application Ser. No. 12/597,008, now U.S. Pat. No. 7,905,683, filed Nov. 11, 2009, which claims the benefit under 35 U.S.C. §365 of International Patent Application No. PCT/US2008/061529, filed Apr. 25, 2008, which claims the benefit under 35 §119 of U.S. Provisional Patent Application Ser. No. 60/926,709, filed Apr. 27, 2007, the disclosures of which are all expressly incorporated herein by reference.

FIELD OF THE INVENTION

The current invention provides processes and apparatuses for introducing slurry into underground geological formations thereby beneficially using the slurry to increase methane gas recovery, while also sequestering carbon dioxide from the slurry.

BACKGROUND OF THE INVENTION

Sludge from sewage and wastewater treatment plants represents a serious disposal problem. Currently, sewage sludge is incinerated, disposed of in or used as alternative daily cover in landfills and used as fertilizer. Incineration, however, requires large amounts of fuel because sewage sludge contains a high volume of water, giving it a highly negative heat value. Moreover, use as daily cover in a landfill or fertilizer has disadvantages because sludge generates undesirable odors and can lead to contamination of soil or landfill from, for example, heavy metals or pathogens.

Furthermore, there is a growing wave of public support for renewable energy, popularly called "Green Power." Several well-known companies, according to Power magazine for May 2003, including General Motors, IBM, Dow Chemical and Johnson & Johnson, have announced plans to purchase a portion of their power requirement from "green" sources.

In addition, several state legislatures are requiring power marketers to phase in specific and increasing percentages of power from renewable sources. New York has mandated that state agencies must buy 25% of their power from renewable sources by 2013. Currently 19.3% of the energy produced in New York is generated from renewable sources (New York Public Service Commission). California has passed legislation requiring that 20% of utilities' electricity in the state be produced from renewable sources by 2017. Similar governmental efforts are taking place in Europe and elsewhere.

As the foregoing demonstrates, the disposal of sewage has become increasingly expensive and difficult while at the same time there is a growing need for renewable energy and green power. A need therefore exists for processes and apparatuses to cleanly and economically dispose of sewage.

BRIEF SUMMARY OF THE INVENTION

The current invention provides methods and apparatuses for beneficially using slurry in underground geological formations, while also sequestering carbon dioxide and generating and capturing methane.

DETAILED DESCRIPTION OF THE INVENTION

Figure 1:
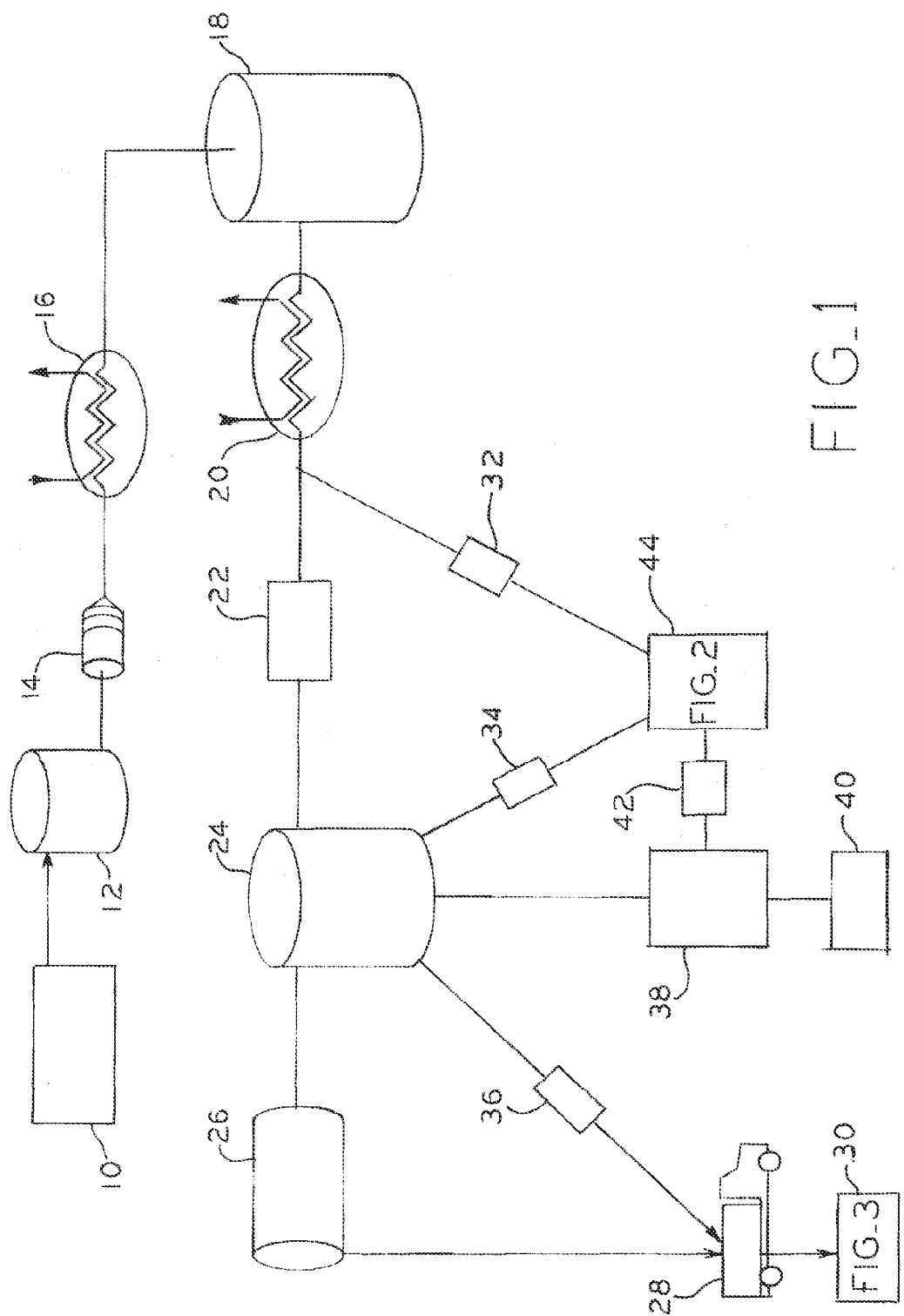
FIG. 1 is a schematic flow diagram illustrating an aspect of the present invention for processing sewage sludge to produce slurry and, optionally, transport of the slurry to a site for introduction into an underground geologic formation.

The current invention provides, for example, processes for conversion of sewage sludge into slurry. In an aspect of the invention, the slurry has viscosity and particle size suitable for introduction into underground geologic formations.

Sewage sludge that is processed into slurry in the present invention may be untreated sewage or sewage that has been treated, for example, by physical, chemical, or biological processes, including anaerobic or aerobic processes. The sewage sludge may also be de-watered to various degrees or otherwise processed prior to being processed into slurry according to the present invention. The sewage sludge can also be mixed with or contain various other ingredients, such as paper mill sludge, food waste and plant matter such as rice hulls, hay straw, discarded cellulosic packaging material, bagasse, green waste, wood and wood waste, clinker or other residue from combustion of wood, palm oil residue and short rotation crops. The sewage sludge can also contain or be mixed with agricultural waste, such as, sewage material obtained from the live stock industry, for example, hog manure, chicken litter or cow manure. The sewage sludge can also contain or be mixed with municipal solid waste, medical waste, paper waste, refuse derived fuels, Kraft Mill black liquor or hydrophilic non-renewable fuels, such as low-rank coals.

According to an aspect of the present invention, sewage sludge is received through means 10, which includes trucks carrying sewage sludge, or conduits, for example, pipes, transporting sewage sludge from a waste water or sewage treatment plant directly to a feed tank 12. Sewage sludge collected in feed tank 12 is optionally processed in device 14 by processes including sieving, screening, mechanical dewatering, mixing with water or a combination thereof, to adjust viscosity or particle size before it is heated, for example, through a heat exchanger 16 to temperature, for example, of about 150° C. to 315° C. (300° F. to 600° F.) under pressure, for example, of about 400 psi to 1200 psi, so that water in the slurry is maintained in liquid phase. In a further aspect of the invention, the slurry is heated under pressure and at a temperature at which the cell walls rupture and a significant molecular rearrangement of the cells occurs, splitting off of a substantial proportion of its oxygen as carbon dioxide. This further aspect results in an additional reduction in viscosity of the slurry. The process of rupturing the cell structure and splitting off carbon dioxide is referred to as decarboxylation, whereas, the process of conversion of cellular constituents to char is referred to as carbonization. The temperature designed to achieve varying degrees of decarboxylation and carbonization is, for example, above 177° C., with a higher temperature resulting in more complete decarboxylation and carbonization. Additionally, such conditions free anions bound cations, such as sodium and potassium, making such atoms and molecules accessible to aqueous dissolution and subsequent removal or disposal.

Heated slurry is optionally given further heat treatment under pressure in the reactor 18, which provides additional time for the rupture of biological cells, decarboxylation and carbonization.

A further aspect of the current invention involves separating water from the slurry by dewatering, for example, by centrifugation. In an aspect of the invention, the solid to water contents of dewatered slurry ranges from about 30% to about 50%.

In a further aspect of the invention, the slurry processed, in whole or in part, as described above, has a viscosity in a range of 30-2600 centipoise (cP), 30-120 cP, 120-170 cP, 170-260 cP, 260-750 cP, 750-1200 cP, 1200-1650 cP or 1650 to 2600 cP, and a solid to water content (solid content) in a range of 10-50%, 20-30% or 30-50%. In a further aspect of the invention, at least 95% of the particles in the slurry are less than 200 micrometers or less than 150 micrometers. In a further aspect of the invention, at least 50% of the particles in the slurry are less than 50 micrometers, 20 micrometers or 10 micrometers. The invention further includes slurry having any combination of these ranges of viscosity, solid content or particle size.

In an aspect of the invention, the slurry processed in the reactor 18 is cooled to a temperature of approximately 35° C.-60° C. (95° F.-140° F.). After being cooled to a desired temperature, the slurry can be directly transported through route 32 to a site for introduction into an underground geologic formation 44. Route 32 includes trucking, pumping or transporting slurry under pressure to the site where slurry is introduced into the underground geologic formation. In an embodiment where the slurry is transported under pressure, the pressure optionally may be used to facilitate the introduction of the slurry into the underground geologic formation. In a further aspect of the invention, the slurry is introduced under pressure into an underground geologic formation at a location next to or near the site where the sewage sludge is processed into the slurry. In a further aspect of the invention, the pressure from the processing of the sewage sludge into the slurry can be used, without a pressure let down or with a reduced pressure let down, to facilitate introduction of the slurry into the underground geologic formation.

Optionally, after being cooled to a desired temperature, the slurry is subjected to pressure let-down in separator 22. The reduction in pressure that occurs in separator 22 can be used to release carbon dioxide dissolved in the slurry. Carbon dioxide that is released from the slurry upon pressure let-down is collected and is freed from water vapors by condensation of the vapors into water. Carbon dioxide so collected can be optionally sequestered into underground geologic formations by first dissolving the carbon dioxide in water or another suitable liquid and then under pressure, to prevent release of the carbon dioxide, introducing the liquid into the underground geologic formation. Furthermore, carbon dioxide so collected can also be used for other purposes after optional purification.

Slurry is then optionally stored in storage tank 24, from which it can be processed. Slurry from storage tank 24, can optionally be transported through route 34 to the site for introduction into the underground geologic formation 44. Route 34 includes trucking, pumping or transporting the slurry to the site for introduction of the slurry into the underground geologic formation.

In an alternate embodiment, the slurry from storage tank 24 is mixed, for example, in tank 38, with a microbial inoculum, for example, from reservoir 40. Slurry mixed with the microbial inoculum can then be transported, through route 42, to the site for introduction into the underground geologic formation 44. Route 42 includes trucking, pumping or transporting slurry to the site where the slurry is introduced into the underground geologic formation.

In a further aspect of the invention, slurry from storage tank 24 is transported to truck 28 via either of alternate route 36 or step 26 which involves dewatering or drying of slurry. Alternate route 36 includes trucking, pumping or transporting the slurry from storage tank 24 to trucks 28. Dewatering or drying devices used for step 26 include thickeners, hydroclones, centrifuges, pressure and vacuum rotary filters, horizontal filters, belt and rotary presses or any combination thereof.

Figure 2:
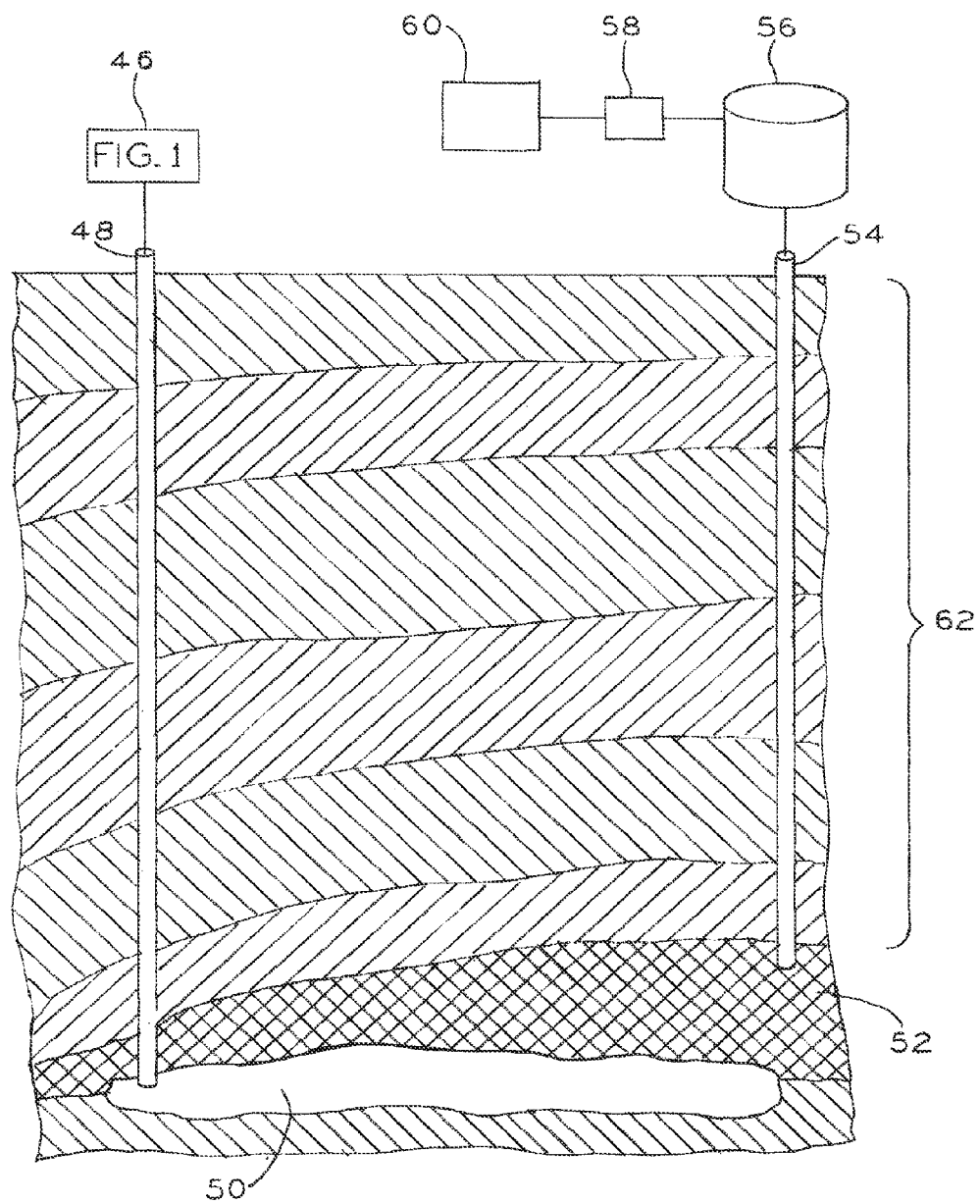
FIG. 2 is a schematic flow diagram illustrating an aspect of the present invention for the introduction of slurry into an underground geologic formation for digestion of the slurry and generation of methane from the slurry in the formation and further collection, purification and use of the generated methane.
Figure 3:
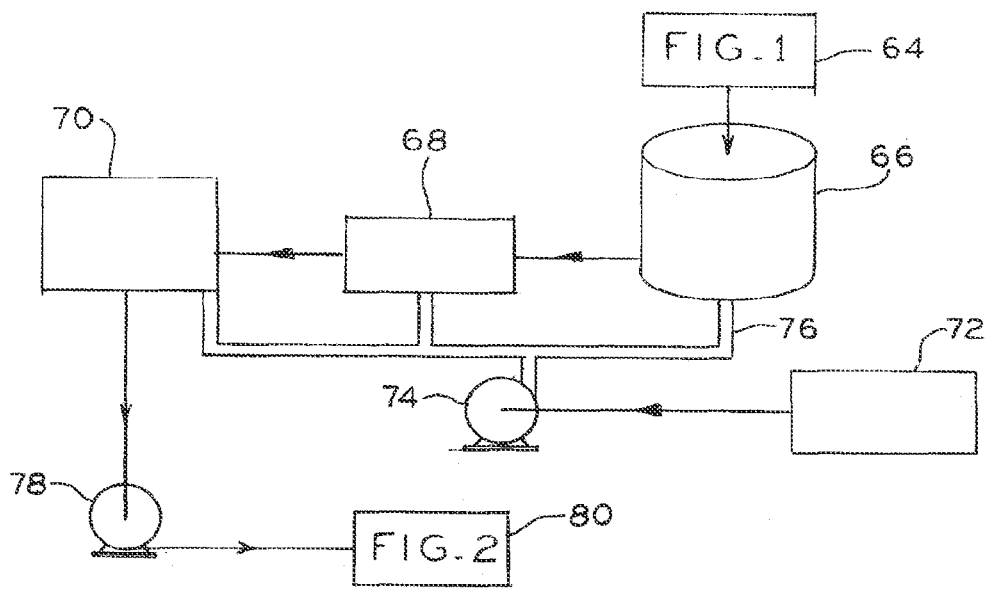
FIG. 3 is a schematic flow diagram illustrating optional processing of slurry prior to the slurry's introduction into an underground geologic formation.

Trucks 28 can deliver the slurry which may be dewatered or dried in step 26, either to the site for introduction of the slurry into the formation, for example, an injection well 48 of FIG. 2 or to the receiving tank 66 of FIG. 3. Slurry from the receiving tank 66 is transported to mixing units 70 via augers 68. Optionally, water from water source 72 is pumped by water pump 74 through pipes 76 in one or more of the receiving tank, augers or mixing unit. A microbial inoculum can optionally be mixed with the slurry in mixing unit 70. Slurry, optionally mixed with water or microbial inoculum, is transported through placement pump 78 to the site for introduction of the slurry into the formation, for example, an injection well 48 of FIG. 2.

Figure 4:
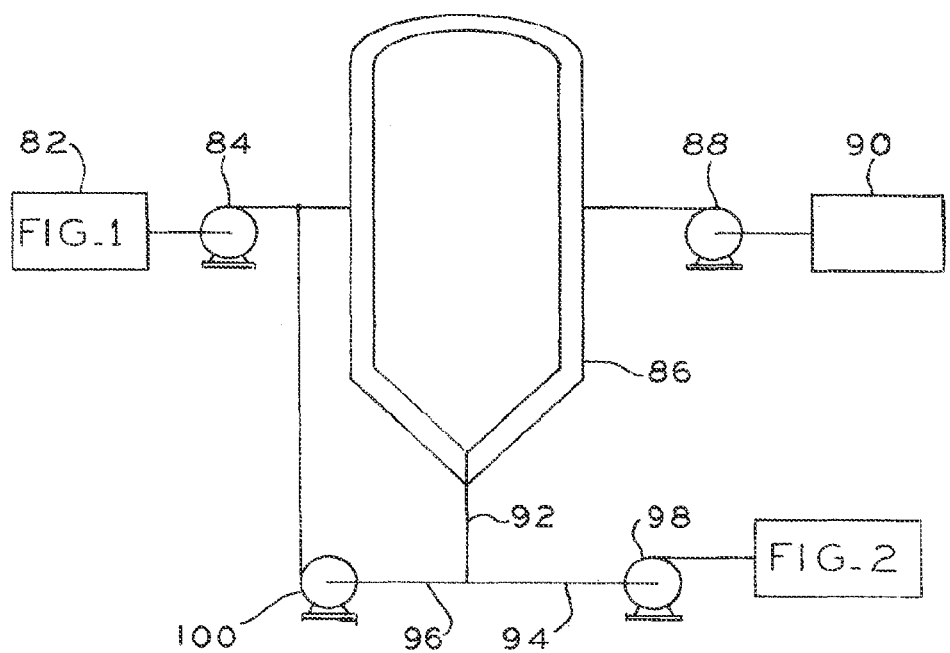
FIG. 4 is a schematic flow diagram illustrating storage of slurry, addition of microbial inoculum to the slurry and conveyance of the slurry to a site for introduction into an underground geological formation.

Alternately, from any of alternate routes 32, 34, 42, or 28 of FIG. 1, the slurry can be pumped to silo 86 of FIG. 4 via pump 84. The storage silo 86 may be insulated to reduce heat loss and may be heat traced to maintain the temperature in appropriate digestion range. Optionally, microbial inoculum from reservoir 90 can also be introduced by pump 88 to silo 86 wherein the microbial culture is mixed with the slurry. The reacted slurry is circulated via pump 100 to maintain solids in the slurry in suspension. The slurry from silo 86 can be transported through means of transporting the slurry 92 and 94 and pump 98 to the site for introduction of the slurry into the formation, for example, an injection well 48 of FIG. 2.

In another aspect of the invention, from any of the alternate routes 32, 34, 42, or 28 of FIG. 1, placement pump 78 of FIG. 3, or pump 98 of FIG. 4, the slurry is received at the site for introduction of the slurry into the formation, for example, an injection well 48 of FIG. 2, where the slurry is introduced into the underground geologic formation 50.

In another aspect of the current invention, as discussed above, the pressure may be decreased after the slurry is treated with increased pressure and temperature in a step referred to as pressure let-down. Optionally, however, the step of pressure let down is eliminated or reduced, and the pressure of the slurry can be used to aid in the introduction of the slurry into the underground geologic formation.

Furthermore, also as discussed above, the slurry may be dewatered, by for example, mechanical dewatering by centrifugation or dewatering by drying, can be eliminated or reduced and the slurry can be introduced into the underground geologic formation without dewatering or after partial or incomplete dewatering.

Furthermore, because the current invention can process undigested or digested sewage sludge, it provides an additional opportunity to achieve significant savings by eliminating or reducing treatment for reducing pathogens.

Additionally, the present invention may be used to reduce odor emissions associated with sewage sludge treatment, handling and disposal. This is because, in an aspect of the invention, the sewage sludge may be processed into slurry in piping or closed conveyance apparatuses and then introduced into deep underground geologic formations, thereby significantly reducing the emission of odors above ground.

Further aspects of the invention include:
1) Heating of the sewage sludge with indirect heat transfer using heat exchangers or by direct injection of steam.
2) Controlling the slurry reaction to maximize viscosity reduction and the break down of fibrous materials that would cause clogging in introducing the slurry to underground geologic formations and regulate temperature or pressure of the reaction to produce slurry with a desired amount of cellular break down, decarboxylation or charring. A further aspect of the invention involves treating the slurry at a reduced temperature and pressure so as to produce only partial breakdown of cellular constituents, partial decarboxylation and partial carbonization. A further aspect of the invention involves treating the slurry at a temperature and pressure designed to destroy human pathogens. A further aspect of the invention involves heating sewage sludge under pressure, optionally, in the presence of an alkali, to a temperature at which a significant physical and molecular rearrangement occurs that is characterized by splitting off a substantial proportion of the oxygen bound in the carbonaceous waste as carbon dioxide. As a result, in this aspect, solid particles in the sewage sludge lose much of their fibrous and hydrophilic character, and are broken down into smaller particles of carbonized organics or char, resulting in a slurry of dramatically improved rheology, i.e., capable of a much higher solids concentration (or energy density) at processable viscosities. Simultaneously, cation and anion impurities, like sodium, potassium, chlorine, sulfur, nitrogen, toxic metals, and others, are significantly reduced in the resulting slurry.
3) Lowering the temperature of the reacted slurry, for example, slurry exiting a slurry cooler or flash tank, to 35° C.-60° C. (95° F.-140° F.). In a further aspect, the slurry is cooled to microbial mesophilic or thermophilic temperatures, for example, 15-25° C. for mesophilic microbes or 25-45° C. for thermophilic microbes. Cooling the reacted slurry to mesophilic or thermophilic temperatures make conditions suitable for the slurry to be inoculated with such microorganisms, which in an aspect of the invention may be used to enhance the digestion and generation of methane from the slurry. Furthermore, such temperature ranges may be used to increase the adjustment of the microbes to the slurry environment, thereby facilitating their proliferation upon introduction of the slurry into underground geologic formations.

In a further aspect of the invention, a microbial inoculum can be mixed with the slurry at various steps as described above and alternately it can be introduced separately from the slurry to the underground geologic formation. Microbial inoculum mixed with slurry or introduced directly into the underground geologic formation may comprise a culture of single micro-organism, a known mixture of or consortium of microbes or raw primary sludge (which contains a large quantity and wide diversity of microbes useful for the digestion and methane generation from the slurry). Examples of microorganisms that can be used as inoculum include archaebacteria, anaerobes, halophiles, mesophiles, thermophiles, facultative anaerobes and mixtures thereof. Optionally, the microorganisms used as inoculum may be genetically engineered. Furthermore, in an aspect of the invention, chemicals are added such as calcium sulfate that stimulate the digestion of the slurry or methanogenesis therefrom. Alternately, digestion of the slurry and methanogenesis can be stimulated by introduction into the slurry of carbon monoxide in order to purge air out of the slurry and create anaerobic conditions. Carbon monoxide can be introduced along with water or nutrient solutions. Other chemicals may be added to adjust pH and alkalinity to optimize proliferation of the microorganisms.

Regarding the slurry reaction process, in an aspect of the invention, sewage sludge is received from various sources, for example, wastewater or sewage treatment plant and into a raw feed tank. Optionally, polymer may be added as a flocculant or water may be added to adjust the viscosity of sewage sludge. Further the sewage sludge may be treated with heat or shearing or grinding or screening in order to adjust the viscosity and particle size suitable for further processing and chelating agents or other chemicals may be added to remove phosphorous or other chemicals from sewage sludge. In a further aspect of the invention, the sludge is preheated to about 150° C. to 315° C. (300° F. to 600° F.) under pressure ranging from 250 to 1600 psi before the resulting slurry is conveyed into a reactor. In the reactor, the slurry is heated under pressure at a temperature which causes the biological cells to rupture thereby releasing the water trapped inside the cells and, optionally, causes complete or substantially complete decarboxylation of cell constituents and converts the cell constituents to char.

The process for obtaining slurry from sewages sludge further includes the processes described in U.S. Patent Application Publication number US 2006/0096163 and PCT Patent Application Publication number WO 06053020, both of which are entitled "Slurry dewatering and conversion of biosolids to a renewable fuel." The contents of these publications are expressly incorporated herein by reference in their entirety.

A further aspect of the current invention involves preparation of slurry having particle sizes suitable for introduction of the slurry into underground geologic formations. In an aspect of the invention, in introducing the slurry into underground geological formations, the particle size of the slurry is small, for example, in the order of micrometers. Such particle size reduces blockage or damage to pipes or machinery used for introduction of the slurry into the formation and facilitates the flow of the slurry through pores and fractures in the underground geologic formation by reducing blockage of pores and fractures, thereby avoiding the loss of underground space and maximizing the amount of slurry that can be introduced in a particular underground geologic formation. Furthermore, small particle size enhances rheology of the slurry, that is, it enhances the properties of the slurry to maintain low viscosity at high solid concentration.

A further aspect of the current invention involves preparing slurry with a viscosity suitable for introduction into underground geologic formations and at the same increasing the percentage of solids in the slurry. This results in reducing the space taken up by slurry water in the underground geologic formation, maximizing the amount of solids introduced into the particular underground geologic formation and thereby increasing the amount of methane production potential of the introduced slurry.

In a further aspect of the invention the slurry introduced into the formation has the following properties: a viscosity in a range of 30-2600 cP, 30-120 cP, 120-170 cP, 170-260 cP, 260-750 cP, 750-1200 cP, 1200-1650 cP or 1650 to 2600 cP; a solid content in a range of 10-50%, 20-30% or 30-50%; at least 95% of particles in the slurry having a size less than 300 micrometers; or at least 50% of the particles in the slurry having a size less than 150 micrometers, 50 micrometers or 20 micrometers. The foregoing parameters are measured, for example, at a wellhead where the slurry is introduced into the formation, but also can be measured at other places along the apparatuses used for the introduction of the slurry into the underground geologic formations, for examples, at various locations along the pipes used for introduction of the slurry into the underground geologic formation. The present invention includes all combination of the above mentioned ranges of the slurry viscosity, particle size or solid content. However, as can be envisioned by a skilled artisan, the desired combination of slurry viscosity, solid content or the particle size in the slurry will be determined by other aspects of the invention, for example, the apparatuses used for the introduction of the slurry into underground geologic formations, or the configuration of the underground geologic formation.

In a further aspect of the invention, the centrate produced upon centrifugation of the reacted slurry, is introduced in to the underground geologic formation. The centrate produced from the centrifugation of the reacted slurry has a solid content of between 0.5 to 3%.

In a further aspect of the invention, the process of the current invention can reduce viscosity of sewage sludge by up to three orders of magnitude, which combined with the other benefits, such as viscosity and particle size lowering and organic molecule breakdown, permits the slurry to flow freely at much higher solids concentrations within the underground geologic formation.

An even further aspect of the invention involves production of slurry which is psuedoplastic. With psuedoplastic slurry, when pressure is increased, viscosity decreases. This aspect of the current invention facilitates introduction of the slurry into underground geologic formation under pressure.

Introduction of the slurry to underground geologic formations can be performed by any of a number of different methods. Examples of methods by which the slurry can be introduced into underground geologic formations include pumping, injecting under pressure, allowing the slurry to flow under gravity or using the pressure used for preparation of the slurry to introduce the slurry into underground geologic formations. Another example of a process for introducing the slurry into an underground geological formation, is slurry injection technology, which may be used to introduce the slurry into a formation using drilling equipment.

The underground geologic formation selected for introduction of the slurry may be a natural oil or gas well, from which oil or gas is completely or partially removed, thereby creating an underground empty space or may be other depleted underground reservoirs. Advantages of selection of such underground geologic formation for the current invention include that such underground geologic formation provides abundant underground space for introducing the slurry, such underground site may be overlain by a suitable methane accumulation zone which facilitates collection of methane produced via digestion of the slurry and methanogenesis therefrom. Such a formation may also contain a natural consortium of suitable micro-organisms for conversion of the slurry to methane.

A further aspect of the invention involves selection of an underground geological formation comprising underground empty space that is produced via natural geological activities. In a further aspect of the invention, the underground geologic formation comprises a geologic stratum containing pores or fractures. A porous stratum is, for example, a stratum formed of porous geologic material, such as porous rocks or sand that provides empty space within the stratum. A stratum containing pores or fractures provides subterranean space for the slurry.

In a further aspect of the invention, the porous or fractured stratum is sandwiched by impermeable or non-porous strata. This arrangement of strata reduces leeching of the slurry and escape of methane into neighboring geologic strata. A further aspect of the invention involves selection of the underground geologic formation comprising alternate layers of porous or fractured strata and non-porous or impermeable strata. Such an arrangement of porous or fractured strata with non-porous or impermeable strata provides additional reduction of leeching of slurry and escape of methane.

A further aspect of the invention involves production of fractures in the underground geologic formation by, for example, introducing the slurry under pressure, to generate the fractures. This provides additional space for slurry in the existing formation, thereby reducing the need for search for or selection of additional underground geologic formations. In a further aspect of the invention, the formation of fractures is regulated in order to reduce the creation of fractures that permit leaching of slurry or escape of methane.

A further aspect of the invention, therefore, involves selection of the underground geologic formation for the slurry introduction process of the current invention so that underground sources of drinking water or oil or other valuable underground reservoirs are not contaminated with the introduced slurry.

An aspect of the invention involves monitoring the process of introduction of the slurry into the underground geologic formation, for example, monitoring wellhead and bottom hole pressure, surface deformation at the underground geologic formation and the integrity of the surrounding rock formations. Such monitoring of the slurry introduction may be used to improve the efficiency of the slurry introduction process, such as, the optimal rate and amount of slurry introduced. Such monitoring also may be used to detect technical difficulties in the slurry introduction process, such as, excessive pressure buildup or undesired fracturing.

Slurry introduction can be carried out continuously or in series of discrete introduction operations. An example of continuous operation of the invention involves receipt of sewage sludge, treating sewage sludge by the process of the current invention to produce slurry and introduction into an underground geologic formations located next to or near the site of slurry processing, each step being performed, optionally in a continuous or non-continuous manner.

In a further aspect of the invention, methane generation from the slurry can be carried out for long durations of time, thereby increasing the amount of methane production from sewage sludge and permitting an increased degradation and disposal of sewage sludge. Regarding the collection of methane from the underground geological formation, upon the generation of methane from the slurry, the methane moves upwards and, in an aspect of the invention, is trapped in the methane collection zone 52. Methane collection zone can be produced by specifically installed cased or cemented wells or enclosures made of impermeable material that produces a cavity for collection of methane generated by digestion of the slurry. Gaseous carbon dioxide contamination present in methane generated by digestion of the slurry dissolves in brine water which may be present in the underground geologic formation or in the overlying strata, thereby separating carbon dioxide.

Methane collected in methane collection zone 52 is, for example, conveyed to a methane storage area 56 via a production well 54. Conduits or other machinery used for collection of methane from methane collection area can be placed at different levels in the zone in order to tap methane collected at different levels in the methane collection zone. Optionally, means for moving the conduits or pipes used for collection of the methane can be provided so that the pipes or conduits can be adjusted to different heights within the collection zone. Methane can be stored in methane storage area 56 at high pressure or in a liquid state in order to maximize the use of available space for storage of higher amounts of methane.

In a further aspect of the invention, methane collected in methane collection area can be used in a number of different ways in methane use area 60, after optional purification of stored methane through embodiments for methane purification 58. Embodiments for methane purification include water or steam scrubber, selective absorption of specific contaminant gases by specialized adsorbants, passing through carbon dessicants to remove moisture which may be present in the generated methane, removal of hydrogen sulfide contaminant by treatment of collected methane with oxygen to produce water and elemental sulfur, or treating the collected methane with hydrated ferric oxide to remove hydrogen sulfide contaminant as iron sulfide, removing heavy hydrocarbon by treatment with activated carbon, removing siloxanes by passing the collected methane over a bed of activated carbon or activated graphite, passing collected methane through molecular sieves that can filter methane gas from nitrogen and oxygen or other gaseous impurities.

Methane collected in the present invention can be used as a fuel for power generation systems as a clean energy source, household consumers for home use, industrial users for industrial use, in methane burning electricity generation system, in oil refinery as a fuel to replace heavy oil or as fuel for operating the slurry processing described herein.

EXAMPLES

Example 1

Sewage sludge was subjected to slurry treatment as described in the current invention. The following table indicates viscosity of the resulting slurry at 177° F. and at variable shear rates:

| Shear Rate (sec$^{-1}$) | Viscosity (cP) |
| --- | --- |
| 1.53 | 1073 |
| 3.06 | 644 |
| 5.11 | 442 |
| 10.21 | 265 |
| 51.07 | 81 |
| 102.12 | 49 |
| 153.21 | 36 |
| 170.23 | 33 |
| 306.41 | 22 |
| 340.46 | 20 |
| 510.69 | 15 |
| 1021.38 | 9 |

Example 2

Sewage sludge from a wastewater treatment plant is received in a receiving tank. Sewage sludge is treated in order to adjust the particle size and viscosity by mixing and optionally, addition of water, to produce unreacted slurry. The slurry is then preheated through heat exchangers at a temperature of about 150° C. to 315° C. under pressure of about 400 psi to 1200 psi which is sufficient to keep the water present in the slurry in liquid state.

Preheated slurry is then held at a temperature of about 150° C. to 315° C. under pressure of about 400 psi to 1200 psi in the reactor, which causes rupturing of biological cells and release of the water trapped in the cells. The slurry is then subjected to a pressure let-down which causes carbon dioxide to released from the slurry as a gas. The carbon dioxide is collected.

The slurry is cooled to a temperature of about 35-60° C. and is inoculated with the microbial inoculum. Upon mixing with the microbial inoculum, the slurry is piped directly into an underground geologic formation. Furthermore, the collected carbon dioxide is sequestered into the formation. Methane produced by the digestion of the slurry in the formation is collected in methane collection zone.

Methane collected in purified and used as a source of fuel for operation of the plant that carries out the processes described in the current invention.

Example 3

Sewage sludge was subjected to slurry treatment as described herein. The following table shows the distribution of the particle size in the resulting slurry:

| Slurry particle size (micrometers) | Percent of slurry under the particle size |
| --- | --- |
| 149 | 96 |
| 74 | 83 |
| 53 | 76 |
| 44 | 71 |
| 37 | 68 |
| 25 | 60 |
| 20 | 55 |
| 15 | 49 |
| 10 | 40 |
| 5 | 22 |
| 3 | 10 |

The examples above and the descriptions herein are representative of the apparatuses and processes of the present invention and are not intended to limit the invention.

As used herein, the following terms have the following meanings. "Comprising" or "comprises" means including, without limitation. "Including" or "includes" means including, without limitation. "Or" means and/or.

What is claimed is:
1. A method comprising:
    (a) introducing a slurry into an underground geological formation under conditions such that the slurry produces methane; and
    (b) collecting the methane; wherein
    (c) the slurry introduced into the underground geological formation is obtained from sewage sludge that has been processed with sufficient heat at a temperature of between 150° C. to 315° C. and pressure of between 400 psi to 1200 psi in order to:
        (1) rupture biological cells contained in the sewage sludge, thereby freeing water trapped in the cells, reducing the viscosity of the sewage sludge such that the slurry has a viscosity between 30 cP and 2600 cP, and reducing the size of particles contained in the sewage sludge such that at least 95% of particles contained in the slurry are less than 300 micrometers in size; and
        (2) reduce the amount of water in the sewage sludge converted to steam during the processing.
2. The method of claim 1, wherein the solid to water content of the slurry introduced into the underground geological formation is between 20-30%.

3. The method of claim 1, wherein at least 50% of particles present in the slurry introduced into the underground geological formation are less than 30 micrometers in size.

4. The method of claim 1, wherein the slurry is introduced into the underground geological formation at a predetermined pressure and temperature.

5. The method of claim 4, wherein the predetermined temperature is between 35-60° C.

6. The method of claim 1, further comprising adding microbes to the slurry.

7. The method of claim 1, wherein carbon dioxide contained in or produced by digestion of the slurry is sequestered into the underground geologic formation.

8. The method of claim 1, wherein the collected methane gas is stored.

9. The method of claim 1, wherein the methane gas is used as a fuel for the processing step (c).

10. The method of claim 1, wherein the solid to water content, viscosity, particle size or temperature is measured at a wellhead at a location where the slurry is introduced into the underground geological formation.

11. The method of claim 1, wherein 50% of particles present in the slurry introduced into the underground geological formation are less than 150 micrometers in size.

12. The method of claim 1, wherein the slurry obtained from the processing step (c) is introduced into the underground geological formation while still under pressure from the processing step (c).

13. The method of claim 1, further comprising the step of cooling the slurry obtained from the processing step (c) before introducing the cooled slurry into the underground geological formation.

14. The method of claim 1, further comprising the step of dewatering or drying the slurry obtained from the processing step (c) before introducing the dewatered or dried slurry into the underground geological formation.

15. The method of claim 1, wherein the introducing step (a) uses the pressure from the processing step (c).

16. The method of claim 13, wherein the cooling step comprises cooling the slurry to a mesophilic temperature between 15-25° C. or a thermophilic temperature between 25-45° C.

17. The method of claim 1, wherein the viscosity is measured at a temperature of 177° C.

18. The method of claim 1, wherein the viscosity is measured at a shear rate between $1.5\ sec^{-1}$-$170.2\ sec^{-1}$.

19. The method of claim 1, wherein the solid to water content of the slurry introduced into the underground geological formation is between 10-50%.

20. A method comprising:
(a) introducing a slurry into an underground geological formation under conditions such that the slurry produces methane; and
(b) collecting the methane; wherein
(c) the slurry introduced into the underground geological formation is obtained from sewage sludge that has been processed at a temperature of between 150° C. to 315° C. and at a pressure sufficient to maintain water in the slurry in liquid phase in order to:
  (1) rupture biological cells contained in the sewage sludge, thereby freeing water trapped in the cells, reducing the viscosity of the sewage sludge such that the slurry has a viscosity between 30 cP and 2600 cP, and reducing the size of particles contained in the sewage sludge; and
  (2) reduce the amount of water in the sewage sludge converted to steam during the processing.

21. A method comprising:
(a) introducing a slurry into an underground geological formation under conditions such that the slurry produces methane; and
(b) collecting the methane; wherein
(c) the slurry introduced into the underground geological formation is obtained from sewage sludge that has been processed at a temperature of between 150° C. to 315° C. and at a pressure sufficient to maintain water in the slurry in liquid phase in order to:
  (1) rupture biological cells contained in the sewage sludge, thereby freeing water trapped in the cells, reducing the viscosity of the sewage sludge, and reducing the size of particles contained in the sewage sludge such that at least 95% of particles contained in the slurry are less than 300 micrometers in size; and
  (2) reduce the amount of water in the sewage sludge converted to steam during the processing.

* * * * *